United States Patent
Hesl et al.

(10) Patent No.: US 7,857,511 B2
(45) Date of Patent: Dec. 28, 2010

(54) STAND FOR AN X-RAY SYSTEM

(75) Inventors: Stefan Hesl, Eschenbach (DE); Rainer Häupl, Krummennaab (DE); Dieter Wöhrl, Kemnath (DE)

(73) Assignee: Siemens Aktiengesellschaft, Munich (DE)

( * ) Notice: Subject to any disclaimer, the term of this patent is extended or adjusted under 35 U.S.C. 154(b) by 6 days.

(21) Appl. No.: 11/667,605

(22) PCT Filed: Nov. 21, 2005

(86) PCT No.: PCT/EP2005/056122

§ 371 (c)(1),
(2), (4) Date: Oct. 5, 2007

(87) PCT Pub. No.: WO2006/056563

PCT Pub. Date: Jun. 1, 2006

(65) Prior Publication Data

US 2008/0159486 A1    Jul. 3, 2008

(30) Foreign Application Priority Data

Nov. 25, 2004 (DE) .................. 10 2004 056 995
Dec. 21, 2004 (DE) .................. 10 2004 061 506

(51) Int. Cl.
*H01J 31/50* (2006.01)
(52) U.S. Cl. ..................... 378/189; 378/197
(58) Field of Classification Search .......... 378/188–198
See application file for complete search history.

(56) References Cited

U.S. PATENT DOCUMENTS 3,373,285 A * 3/1968 Barrett ..................... 378/194
3,373,385 A    3/1968 Kessler (Continued)

FOREIGN PATENT DOCUMENTS

DE    21 54 640 A    5/1972

(Continued)

OTHER PUBLICATIONS

Translation and German Written Opinion, PCT/EP2005/056122.

(Continued)

*Primary Examiner*—Hoon Song
(74) *Attorney, Agent, or Firm*—Brinks, Hofer, Gilson & Lione (57) ABSTRACT

The invention relates to a stand (5) which is especially adapted to support for a digital X-ray detector (4) for an X-ray system (1), and to an X-ray system (1) comprising such a stand (5). The stand (5) comprises a stirrup bolt (6) which is rotatably mounted on a base frame (6) and which comprises a first limb (19) for supporting an X-ray emitter (2) and a second limb (20) for supporting an X-ray detector (4), which is provided on its free end with a detector support (21). The detector support (21) comprises a receiving element (23) which is adapted to captivate the X-ray detector (4) in a predetermined position and which can be swiveled in relation to the stirrup bolt (16) about a swivel axis (24) being parallel or tangential to the horizontal axis (18) and about a rotational axis (25) being perpendicular to the swivel axis (24) and a principal plane (E) of the receiving element (23).

21 Claims, 8 Drawing Sheets

U.S. PATENT DOCUMENTS

| | | | |
|---|---|---|---|
| 3,803,418 A | | 4/1974 | Holstrom |
| 6,412,978 B1 | | 7/2002 | Watanabe et al. |
| 6,431,751 B1 | * | 8/2002 | Everett et al. ............... 378/197 |
| 2003/0091152 A1 | * | 5/2003 | Dietz et al. ................. 378/197 |

FOREIGN PATENT DOCUMENTS

| | | |
|---|---|---|
| GB | 1175032 | 12/1969 |
| JP | 58220398 A | 12/1983 |
| JP | 11009579 A | 1/1999 |
| JP | 2000201909 A | 7/2000 |
| WO | WO 80/01111 | 5/1980 |

OTHER PUBLICATIONS

Translation and International Preliminary Report on Patentability for PCT/EP2005/056122.

Translation and German Office Action dated Oct. 20, 2006 for DE 10 2004 061 506.3-54.

* cited by examiner

STAND FOR AN X-RAY SYSTEM

The present patent document is a §371 filing from PCT Application Serial Number PCT/EP2005/056122, filed Nov. 21, 2005, designating the United States, which is hereby incorporated by reference. This patent document also claims the benefit of DE 10 2004 056 995.9, which was filed Nov. 25, 2004, and also DE 10 2004 061 506.3, which was filed Dec. 21, 2004.

BACKGROUND

The present embodiments relate to a stand for an X-ray system and an X-ray system with a stand.

A conventional X-ray system includes a stand that supports an X-ray emitter and a cassette holder. The cassette holder accommodates a film cassette, a storage film or the like. A conventional stand comprises a U-frame which is mounted so as to be capable of rotating about a horizontal axis. The U-frame carries the X-ray emitter on a first limb and the cassette holder on a second limb. The X-ray emitter and the cassette holder are secured in centered opposition with respect to a direction of emission irrespective of the swivel position of the U-frame in the room.

Digital X-ray detectors are beginning to replace the conventional film cassettes. Digital X-ray detectors are becoming increasingly popular. Digital X-ray detectors generate a recorded X-ray image in the form of digital image data. Two-dimensional flat image detectors have become commercially available. The two-dimensional flat image detector can be a mobile device.

SUMMARY

A stand for an X-ray system is suitable for supporting a digital X-ray detector.

In one embodiment, the stand includes a base frame on which a U-frame is mounted so as to be capable of rotating about a horizontal axis. The U-frame includes a first limb for supporting an X-ray emitter and also a second limb. A detector support is attached on the free end of the second limb. The detector support includes a recording element in which a digital X-ray detector designed as a flat image detector can be secured firmly in a predetermined position. The detector support is designed so that the recording element (where relevant together with the X-ray detector secured on same) can be swiveled both about a tilt axis being aligned parallel to the horizontal axis and also about a rotational axis being perpendicular to same. The rotational axis corresponds to a surface normal on a principal plane defined by the direction of extension of the recording element so that this principal plane is invariant in relation to a swiveling of the recording element about the rotational axis. As a result of this, the X-ray detector secured on the recording element is also rotated without its detector surface, which is essentially parallel to the principal plane, being tilted in the room. In an equivalent manner, the detector support can also be fixed on the U-frame in such a way that the tilt axis is aligned tangentially, i.e. perpendicular and at a distance with respect to the horizontal axis.

The dual-axis adjustability of the detector support enables the flexible employment of the X-ray detector for a large number of different recording positions. The X-ray detector can rotate about the rotational axis, and the limited detector surface of the digital X-ray detector can be exploited with respect to the respective recording position.

In one embodiment, the recording element is designed so that the X-ray detector can be secured and removed again without employing tools, such as with one hand. This simplifies the handling of the X-ray system with regard to a mobile employment of the X-ray detector. The X-ray detector can be removed easily from the detector support of the stand and, for example, employed in a separately located Bucky wall stand or utilized for a free recording.

The recording element includes a quantity of clamping elements that grip the X-ray detector on all sides in a securing position. The clamping elements allow the X-ray detector to be secure and be released easily. In one embodiment, a recording element grips a corner of the X-ray detector.

At least one clamping element can be deflected in an elastic manner from a securing position. Alternatively, an operating mechanism deflects one or more of the clamping elements in a reversible manner from their respective securing position.

In one embodiment, the recording element includes a holder. The X-ray detector can be inserted into the holder.

The detector support includes a latch that latches the recording element, so as to be capable of being released, in one of a plurality of swivel positions in the case of a swiveling about the tilt axis and/or in the case of a swiveling about the rotational axis, in order to secure the recording element against an undesired self-initiated rotation. The latch may include a sensitive latch. The sensitive latch generates pressure points when the recording element is swiveled. These pressure points can be overridden with the manual application of a corresponding counter-pressure. Alternatively, the recording element is secured against an unintended self-initiated swiveling by a friction contact that can be manually overridden or by other locking mechanisms that can be released.

The stand includes a ceiling stand. The base frame is designed to be fixed to a ceiling of a room.

In one embodiment, the X-ray system includes a digital X-ray detector and also the stand described in the foregoing that supports the digital X-ray detector. The X-ray system includes a control unit that controls and supplies power to the X-ray detector. The control unit is fixed on the base frame of the stand.

The stand enables the flexible use of the X-ray detector. The control unit on the base frame of the stand saves space and does not hinder the working operations on the X-ray system.

A supply cable connects the control unit to the X-ray detector. The supply cable is routed in a cable guide arranged on the outside with respect to the stand. The supply cable is routed in an orderly manner along the stand in the case of a mobile X-ray detector attached to the stand. The supply cable can be easily disconnected from the stand in the case of the use of the mobile X-ray detector that is away from the stand.

The cable guide includes a retraction facility for the supply cable. The retraction facility automatically draws the supply cable into a rest position that is away from the working area of the X-ray system if the full length of the cable is not needed. The retraction facility can include a self-reeling cable drum and/or a cable pull acting on the supply cable. Additionally or alternatively, the cable guide includes at least one point support. The supply cable can be secured on the stand using the point support. To be able to handle the supply cable flexibly for a mobile utilization of the X-ray detector, said or each point support is designed in such a way that the supply cable can be released from the fixing without tools. Said or each point support can include a magnetic support. Alternatively,

DETAILED DESCRIPTION

Mutually corresponding parts are provided with the same reference symbols in the figures.

Figure 1:
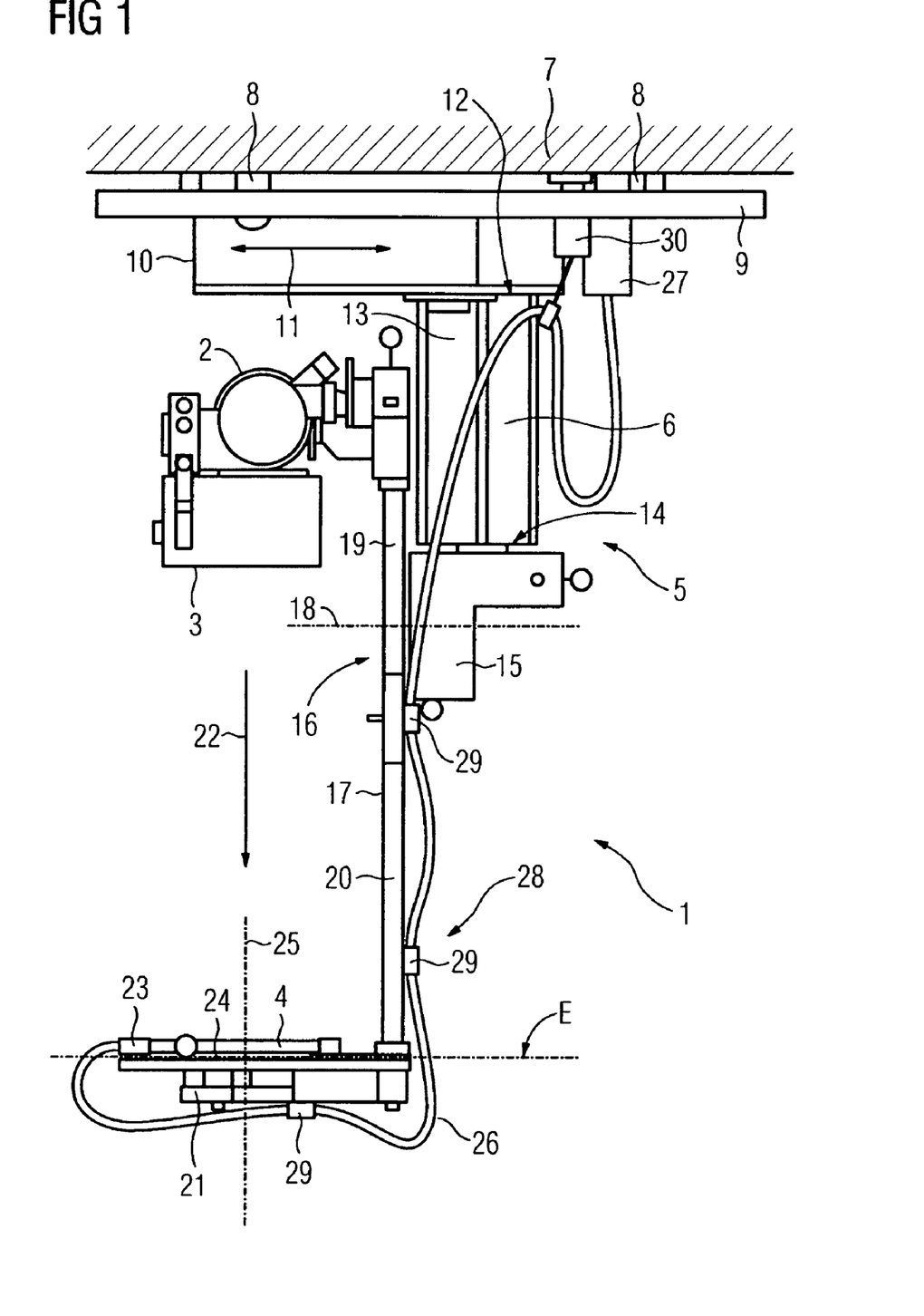
FIG. 1 is a schematic side view of an X-ray system with an X-ray emitter, a digital X-ray detector, and a stand for supporting the X-ray emitter and the X-ray detector.
Figure 2:
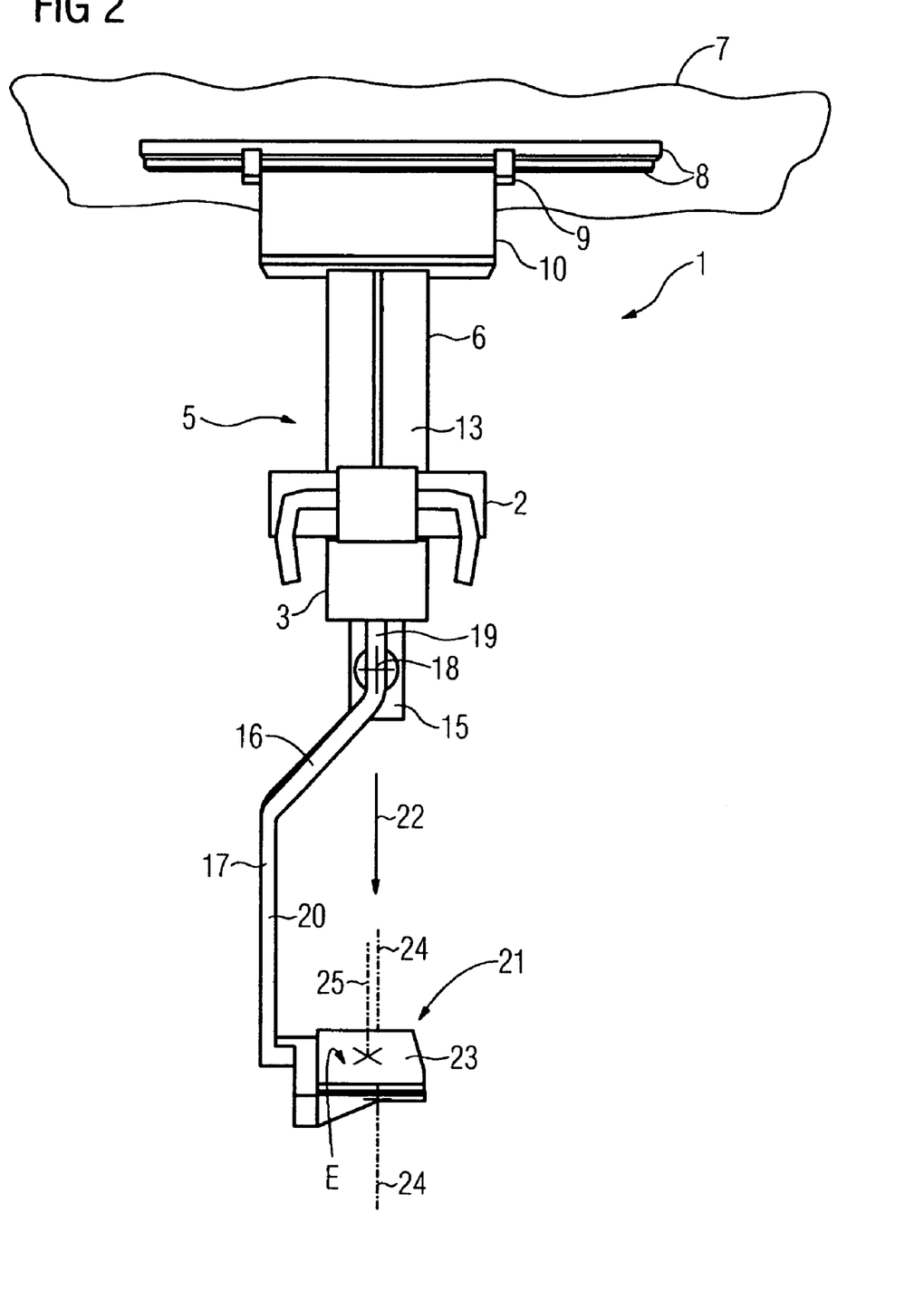
FIG. 2 is a perspective front view of the X-ray system as shown in FIG. 1.

The X-ray system 1, shown in FIGS. 1 and 2, includes an X-ray emitter 2 with a multileaf collimator 3 that is connected in front of the X-ray emitter 2 and a digital X-ray detector 4 designed as a flat image detector (not shown in FIG. 2 for reasons of simplification). The X-ray system 1 includes a stand 5 that supports the X-ray emitter 2 and the X-ray detector 4.

The stand 5 includes a ceiling stand and is fixed to the ceiling 7 of an examination room with a base frame 6. The base frame 6 is suspended so as to be capable of displacement on two longitudinal rails 8 attached to the ceiling 7 of the room. The base frame 6 can be displaced along these longitudinal rails 8 in a direction perpendicular to the plane of the drawing in FIG. 1. The framework of the base frame 6 may also include a transverse track 9 for transverse displacement of a telescopic carriage 10 of the stand 5 in a transverse direction 11 (FIG. 1). An extendable and downward protruding telescopic arm 13 is arranged on a bottom side 12 of the telescopic carriage 10, on the lower end 14 of which telescopic arm is arranged a support arm 15 for mounting a U-frame 16. The height of the stand 5 may be adjusted using the telescopic arm 13.

The U-frame 16 includes a long main beam 17. The long main beam 17 is mounted on the support arm 15 so as to be capable of rotating about a horizontal axis 18, so that the main beam 17 can be swiveled within a vertical swivel plane (not shown in detail). The main beam 17 includes a first limb 19 and a second limb 20. The limbs 19 and 20 abut (connect to) each other in the area of the horizontal axis 18 and protrude from there in roughly opposite directions. The limb 19 carries the X-ray emitter 2 on its free end. The limb 20 carries a detector support 21 on its free end. The detector support 21 is designed to secure the X-ray detector 4 in a predetermined position in which the X-ray detector 4 is located in centered opposition to the X-ray emitter 2, viewed in a direction of emission 22 of the X-ray radiation emitted by the X-ray emitter 2.

The detector support 21 includes a plate-shaped receiving element 23 that secures the X-ray detector 4. The receiving element 23 (with the X-ray detector 4 secured on same where relevant) can be tilted about a tilt axis 24 and also rotated about a rotational axis 25 being perpendicular to same. The detector position is flexibly adapted with regard to the fulfillment of various exposure conditions.

The tilt axis 24 is aligned parallel to the horizontal axis 18. The rotational axis 25 corresponds essentially to the surface normal on the plate-shaped receiving element 23 and also on the detector surface of the X-ray detector 4 secured on same. The rotation of the receiving element 23 about the rotational axis 25 is within a principal plane E established by the receiving element 23 and/or the detector surface of the X-ray detector 4. The detector surface is not tilted in the case of a rotation about the rotational axis 25.

The X-ray detector 4 includes a mobile flat image detector which is secured on the detector support 21 so as to be capable of being released. The X-ray detector 4 can also be employed separately from the stand 5, in particular in a Bucky wall stand (not shown explicitly) or for a free recording.

As shown in FIG. 1, the X-ray detector 4 is connected to a control unit 27 via a supply cable 26. The control unit 27 can be used for the purposes of control and also for the purposes of power supply. The control unit 27 is attached to the base frame 6 in the vicinity of the ceiling, in particular above the head of a user. The control unit 27 is displaced together with the X-ray system 1. The control unit 27 can be withdrawn out of the working area of a user of the X-ray system 1 by the near-ceiling arrangement. The control unit 27 is not in the way of the user during the operation of the X-ray system 1.

The X-ray system 1 includes a cable guide 28. The supply cable 26 is routed along the outside of the stand 5 using the cable guide 28. The cable guide 28 includes a quantity of point supports 29 designed as magnetic supports. The supply cable 26 can be fixed to the detector support 21 and/or the main beam 17 of the U-frame 16, so as to be capable of being released. The cable guide 28 includes a retraction facility 30 designed in the form of a self-reeling cable pull. As shown in FIG. 1, the length of the supply cable 26 not needed for a stand recording is automatically withdrawn into a near-ceiling rest position using the retraction facility 30. If the X-ray detector 4 is employed away from the stand 5, then the supply cable 26 can be pulled out to its full length with a light pull against the retraction facility 30.

Figure 3:
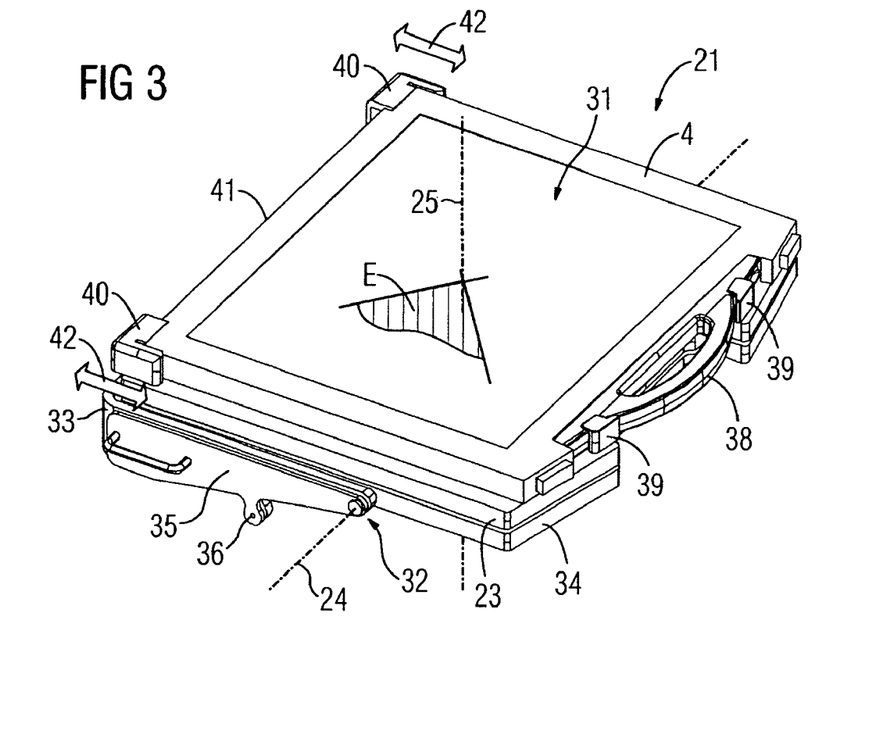
FIG. 3 is a perspective view of a detector support of the stand and the X-ray detector secured on a receiving element of the detector support.
Figure 4:
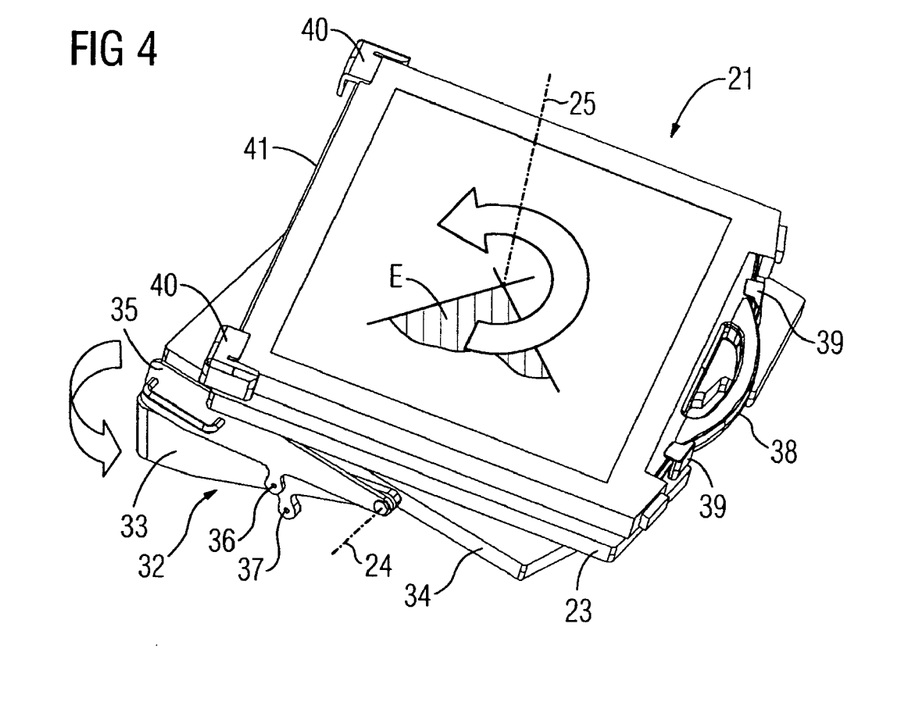
FIG. 4 is a diagram of the detector support in a position of the receiving element that is swiveled about a tilt axis and a rotational axis in relation to FIG. 3.
Figure 5:
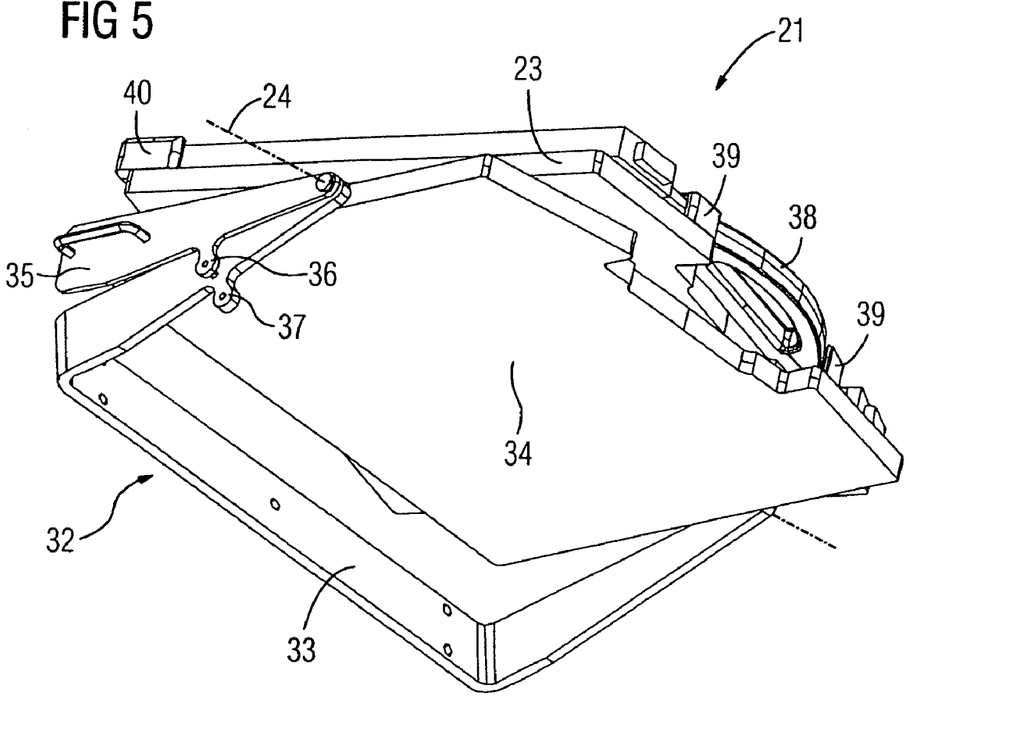
FIG. 5 is a rear side perspective view of the detector support as shown in FIG. 4.

FIG. 3 in an oblique plan view of a top side 31 turned toward the X-ray emitter 2. FIGS. 3, 4 and 5 show the detector support 21 together with the X-ray detector 4 secured on same.

In one embodiment, as shown in FIG. 3, the detector support 21 includes an articulated support element 32. The support element 32 includes a U-shaped support bracket 33 and a support plate 34 mounted on the support bracket 33 so as to be capable of swiveling about the tilt axis 24. The support plate 34 supports the plate-shaped receiving element 23. The receiving element 23 is mounted on the support plate 34 so as to be capable of swiveling about the rotational axis 25 using a collar bushing. As shown in FIG. 2, the support bracket 33 is bolted to the limb 20 of the U-frame 16.

The support plate 34 can be locked with respect to the support bracket 33 in a plurality of swivel positions with respect to the swiveling about the tilt axis 24, in particular 0° (shown in FIG. 2), 15°, and also 30° (shown in FIGS. 3 and 4). As shown in FIGS. 3, 4, and 5, a latching lever 35 can lock the support plate 34 to the support bracket 33. The latching lever 35 is connected to the support plate 34 along the tilt axis 24 so as to be non-rotating. The support plate 34 is latched in each of the predetermined swivel positions by a latching bolt 36 attached to the latching lever 35 engaging in a latching recess 37 corresponding to the respective swivel position. The support plate 34 can be adjusted between various swivel positions when the latching lever 35 is pulled outward at a handle attached on its free end. The latching bolt 36 disengages from the corresponding latching recess 37 so that the support plate 34 can be displaced in relation to the support bracket 33.

A sensitive latch is allocated to the rotation of the receiving element 23 in relation to the support plate 34. The support plate 34 secures the receiving element 23 in a plurality of rotational positions against an undesired self-initiated rotation. A manual operating pressure can override this securing. A handle 38 attached to the X-ray detector 4 is used as an actuator. The handle 38 can be used for rotation of the receiving element 23 and the X-ray detector 4 secured on same about the rotational axis 25.

Two clamping elements 39 and also two further clamping elements 40 can secure the X-ray detector 4 on the receiving element 23 The clamping elements 39, 40 hold the X-ray detector 4 firmly by gripping the receiving element 23. The clamping elements 39 are permanently anchored on the receiving element 23 and engage with the X-ray detector 4 on both sides of the handle 38 in the securing position. The clamping elements 40 engage with the corner points of a back edge 41 of the X-ray detector 4 located opposite the handle 38 in the securing position so that the X-ray detector 4 is clasped on all sides by the clamping elements 39 and 40 in the securing position. The clamping elements 40 can be deflected from their securing position, against a spring tension, by the extent of an unlocking path 42 (indicated schematically). The clamping elements 40 can be used to fix and/or remove the X-ray detector 4.

The X-ray detector 4 can be fixed on the detector support 21. The X-ray detector 4 is inserted into the clamping elements 40 with the back edge 41. The clamping elements 40 are deflected by the X-ray detector 4 in such a way that the handle-side edge of the X-ray detector 4 can be inserted under the clamping elements 39. Upon releasing the X-ray detector 4, the detector is locked automatically by the clamping elements 40 returning to their locking position in an elastic manner.

Figure 6:
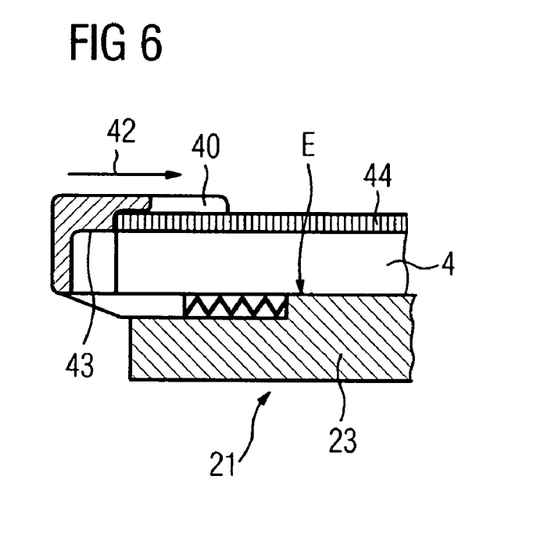
FIG. 6 is a schematic cross section of the X-ray detector being secured together with a scattered radiation grid placed on the top side.
Figure 7:
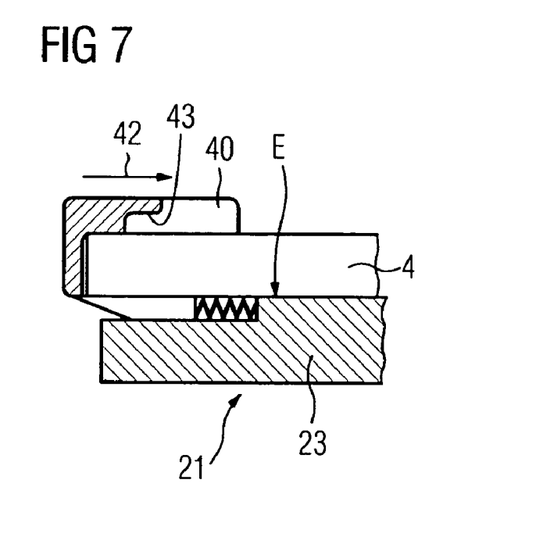
FIG. 7 is a schematic cross section of the X-ray detector being secured without scattered radiation grid.

As shown in FIGS. 6 and 7, the clamping elements 40 have a stepped internal contour 43. The clamping elements 40 can support the X-ray detector 4 optionally with or without a scattered radiation grid 44. The scattered radiation grid 44 can be placed on the top side, securely, for example, without play, on the detector support 21.

Figure 8:
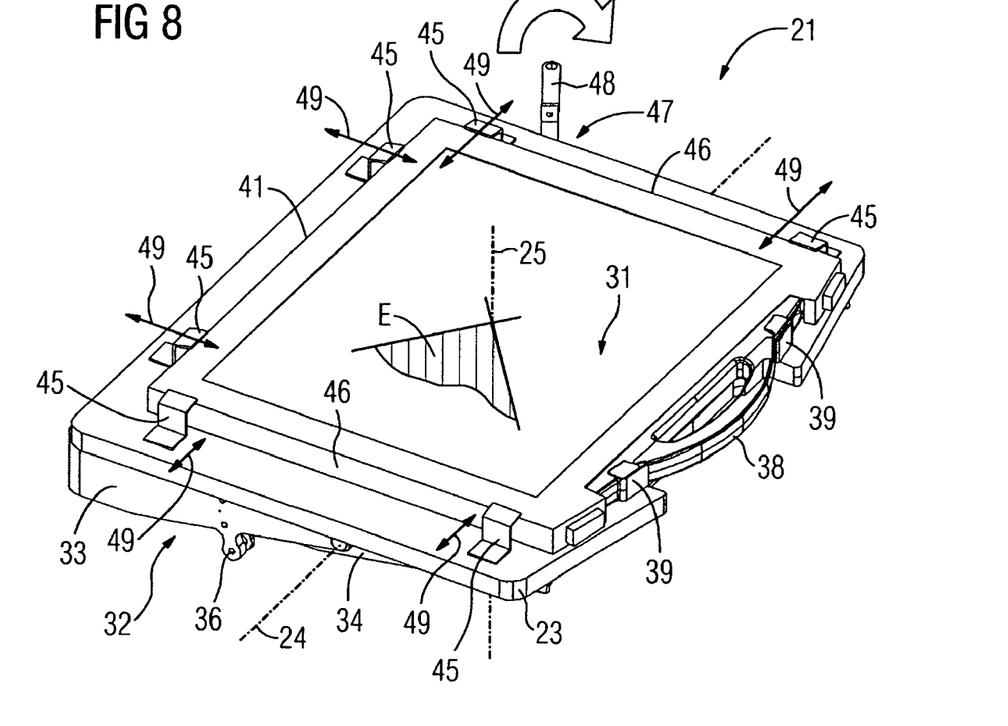
FIG. 8 is a perspective view of an alternative embodiment of the detector support and also the X-ray detector.
Figure 9:
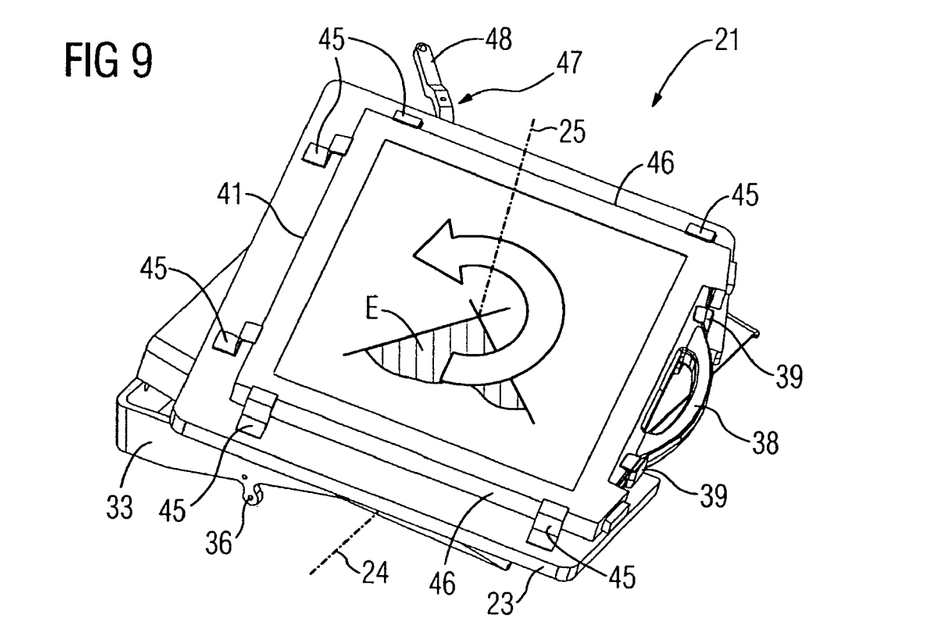
FIG. 9 is a perspective view of the detector support as shown in FIG. 8.
Figure 10:
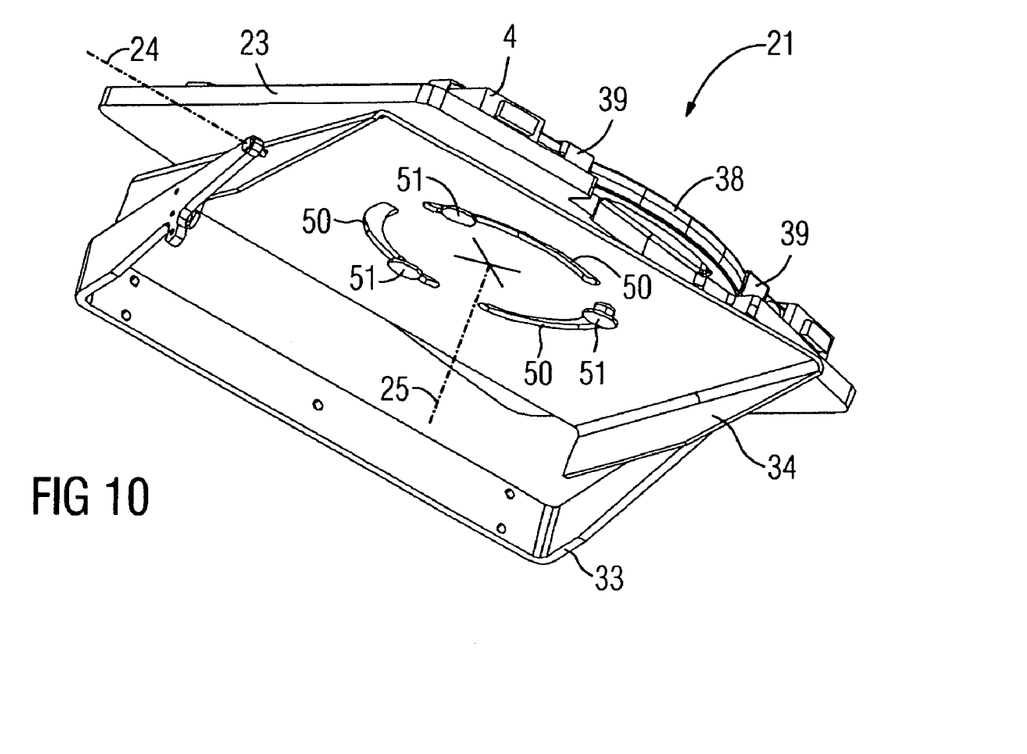
FIG. 10 is a perspective view of the detector support as shown in FIG. 9.
Figure 11:
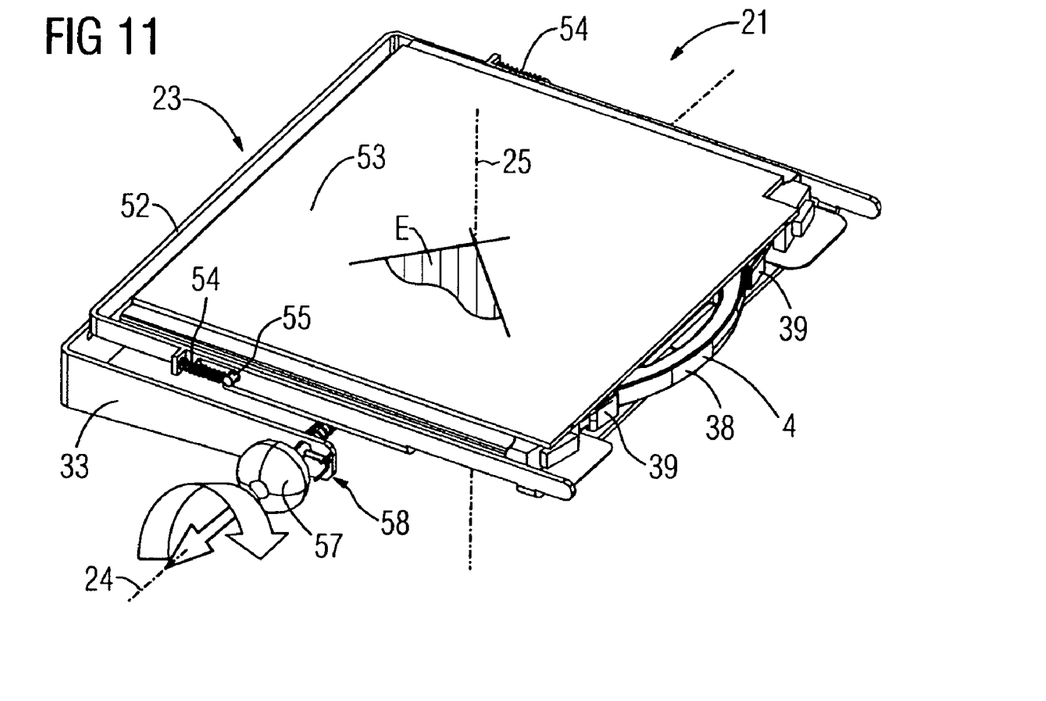
FIG. 11 is a perspective view of another embodiment of the detector support with X-ray detector secured on the detector support.
Figure 12:
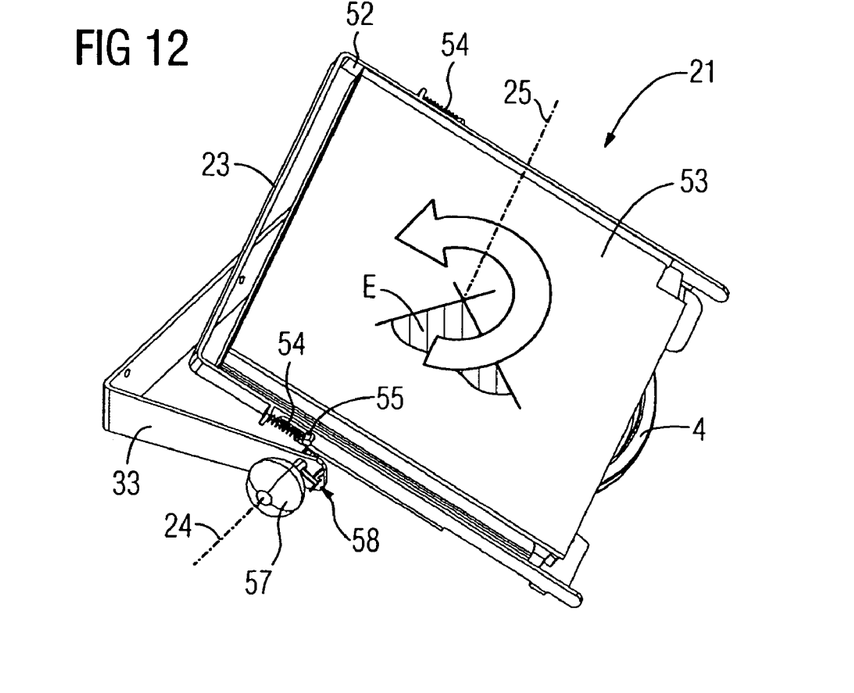
FIG. 12 is a perspective view of the detector support as shown in FIG. 11.
Figure 13:
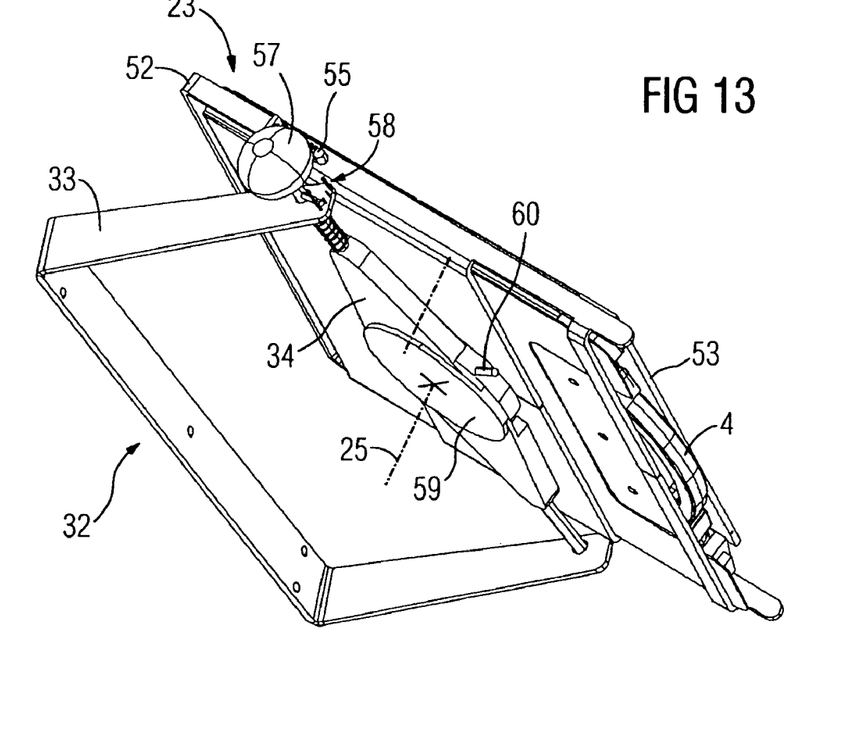
FIG. 13 is a perspective view of the detector support as shown in FIG. 12.

In one embodiment, as shown in FIGS. 8 to 10, modified clamping elements 45 are used instead of the clamping elements 40. The modified clamping elements 45 engage on the back edge 41 and on opposite side edges 46 of the X-ray detector 4. The modified clamping elements 45 and the clamping elements 39 engage on the handle-side and hold the X-ray detector 4 firmly on the receiving element 23 in a securing position. For the purposes of removing the X-ray detector 4, the clamping elements 45 can be displaced, by using an operating mechanism 47. The operating mechanism 47 can be operated via a handle 48, from the securing position along an unlocking path 49 shown schematically (FIG. 8) into a withdrawn release position. The X-ray detector 4 can be removed when the clamping elements 45 are in the withdrawn release position. Operation of the handle 48 in the opposite direction moves the locking elements 45 back into the securing position again. The clamping elements 45 are designed so as to be elastically flexible in order to secure the X-ray detector 4, both with and also without scattered radiation grid 44, without any play.

In one embodiment, as shown in FIGS. 8 to 10, the latching bolt 36 latches the receiving element 23 in various swivel positions with respect to the support bracket 33. The latching bolt 36 is a sensitive latch. The latching bolt 36 can be overridden by manual tilting of the receiving element 23 without a separate locking mechanism having to be operated. The mounting of the receiving element 23 so as to be capable of swiveling about the rotational axis 25 is effected via three annular segment-like slotted holes 50 inserted in the support plate 34 (FIG. 10) in which a corresponding fixing bolt 51 of the receiving element 23 slides in each case.

Figure 14:
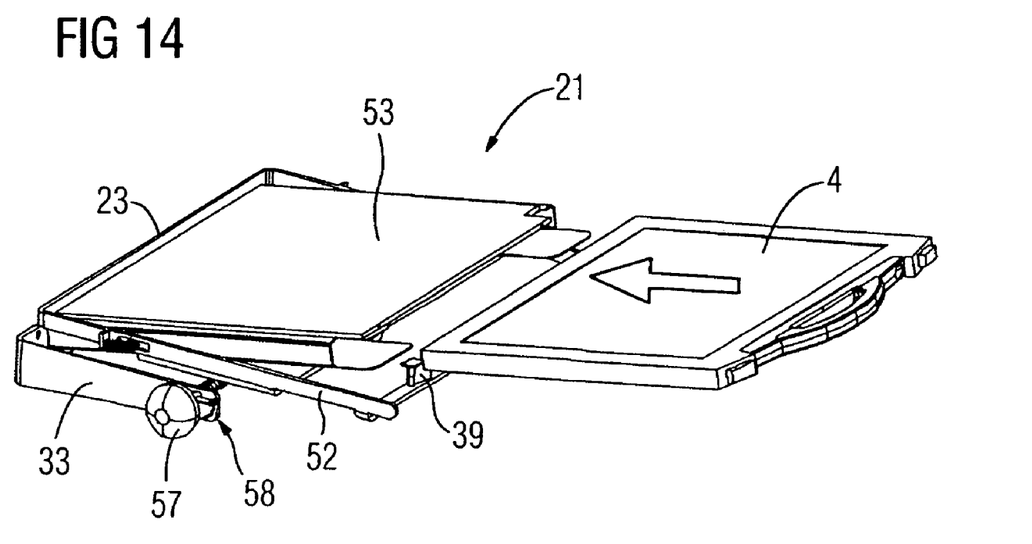
FIG. 14 is a perspective view of the top side of the detector support as shown in FIG. 11 during insertion of the X-ray detector.

In one embodiment, as shown in FIGS. 11 to 14, the receiving element 23 comprises a frame 52 in which a detector holder 53 is supported for accommodating the X-ray detector 4. As shown in FIG. 14, the detector holder 53 can be tilted into an opening position in relation to the frame 52 for the purposes of inserting the X-ray detector 4 into the detector holder 53. Spring elements are optional. The spring elements automatically press the detector holder 53 into this opening position in the absence of the X-ray detector 4 so that the X-ray detector 4 can be inserted at any time. Following the insertion of the X-ray detector 4, the detector holder 53 is pressed manually into a closing position being aligned roughly parallel to the frame 52. Spring elements 54, which engage with a guide bolt 55 securing the detector holder 53 on the frame 52, press the detector holder 53, together with the inserted X-ray detector 4, against the clamping elements 39 permanently attached on the frame 52. The clamping elements 39 gripping the X-ray detector 4 on both sides of the handle 38 hold the detector holder 53 in its closing position and firmly secure the X-ray detector 4 at the same time.

A centering of the X-ray detector 4 within the detector holder 53 is obtained by leaf springs arranged within the detector holder 53. The leaf springs engage with both side edges 46 and optionally with one of the flat sides of the X-ray detector 4. The leaf springs press X-ray detector 4 into a central position within the detector holder 53. The leaf springs ensure that the X-ray detector 4, with or without scattered radiation grid 44, is held securely.

In one embodiment, as shown in FIGS. 11 to 14, a rotary handle 57 can be used to tilt the receiving element 23 about the tilt axis 24. The rotary handle 57 works with a latching facility 58 indicated in FIGS. 11 to 14. The latching facility 58 latches the receiving element 23 and the support plate 34 connected to receiving element 23 in one of a plurality of swivel positions. When unlocking the latching facility 58, the rotary handle 57 is pulled outward along the tilt axis 24 so that the receiving element 23 can be swiveled in relation to the support bracket 33. Upon releasing the rotary handle 57, the latching facility 58 latches in the selected new swivel position of the receiving element 23.

The receiving element 23 and the support plate 34 are connected via a rotary joint 59. The receiving element 23 can swivel about the rotational axis 25 using the rotary joint 59. The rotary joint 59 is provided with a pin 60 (which can be identified in FIG. 13), which, by acting as a stop, limits the rotation of the receiving element 23 in relation to the support plate 34 to a predetermined swivel angle.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. A stand for an X-ray system, the stand comprising:
a base frame; and
a U-frame mounted on the base frame, the U-frame being operable to rotate about a horizontal axis,
wherein the U-frame includes a first limb that supports an X-ray emitter and a second limb that supports a detector support on a free end,
wherein the detector support comprises a receiving element that is operable to secure an X-ray detector in a predetermined position and to swivel in relation to the U-frame about a tilt axis being aligned parallel or tangential to the horizontal axis and about a rotational axis being perpendicular to the tilt axis and a principal plane of the receiving element irrespective of the tilt position of the receiving element,
wherein the detector support further comprises an articulated support element comprising a U-shaped support bracket and a support plate, the support plate being pivotably mounted between the free ends of the support bracket, so that the support plate can be rotated with respect to the support bracket about the tilt axis, the receiving element being pivotably mounted on the support plate, so that the receiving element can be rotated with respect to the support plate about the rotational axis; and
wherein the X-ray detector is operable to be fixed or removed.

2. The stand as claimed in claim 1, wherein the receiving element includes at least one clamping element that is operable to secure the X-ray detector.

3. The stand as claimed in claim 2, wherein at least one clamping element is operable to elastically deflect from a securing position.

4. The stand as claimed in claim 3, wherein the at least one clamping element in the securing position fixes the X-ray detector.

5. The stand as claimed in claim 2, wherein at least one clamping element is operable to be reversibly deflected from a securing position using an operating mechanism.

6. The stand as claimed in claim 5, wherein the X-ray detector is operable to be removed when the at least one clamping element is reversibly deflected.

7. The stand as claimed in claim 1, wherein the receiving element includes a holder, the X-ray detector being insertable into the holder.

8. The stand as claimed in claim 1, wherein the detector support comprises at least one latch that latches the receiving element in one of a plurality of latching positions,
wherein receiving element is operable to be released from the at least one latch.

9. The stand as claimed in claim 1, wherein the X-ray detector is operable to be fixed or removed without tools.

10. The stand as claimed in claim 1, wherein the receiving element comprises a frame to support a holder, and the holder is operable to be tilted into an opening position in relation to the frame.

11. The stand as claimed in claim 10, wherein the holder is operable to be pressed into a closing position aligned roughly parallel to the frame.

12. The stand as claimed in claim 1,
wherein the X-ray system comprises a control unit that is operable to control the X-ray detector, the control unit being fixed on the base frame, and
wherein the control unit and the X-ray detector are connected by a supply cable, the supply cable being routed in a cable guide disposed on the outside of the stand.

13. The stand as claimed in claim 1,
wherein the support bracket is a U-shaped support bracket, and
wherein the receiving element is mounted on the support plate and is operable to be swiveled about the rotational axis.

14. An X-ray system comprising:
a stand comprising a U-frame;
an X-ray detector operable to be secured to a detector support, the detector support comprising a receiving element; and
wherein the receiving element is operable to swivel in relation to the U-frame about a tilt axis being aligned parallel or tangential to the horizontal axis and about a rotational axis being perpendicular to the tilt axis and a principal plane of the receiving element irrespective of the tilt position of the receiving element, and
wherein the detector support further comprises an articulated support element comprising a U-shaped support bracket and a support plate, the support plate being pivotably mounted between the free ends of the support bracket, so that the support plate can be rotated with respect to the support bracket about the tilt axis, the receiving element being pivotably mounted on the support plate, so that the receiving element can be rotated with respect to the support plate about the rotational axis.

15. The X-ray system as claimed in claim 14 further comprising: a control unit that is operable to control the X-ray detector, the control unit being fixed on a base frame of the stand,
wherein the control unit and the X-ray detector are connected by a supply cable, the supply cable being routed in a cable guide disposed on the outside of the stand.

16. The X-ray system as claimed in claim 15, wherein the cable guide comprises a retraction facility that is operable to automatically retract the supply cable into a rest position.

17. The X-ray system as claimed in claim 15, wherein the cable guide comprises at least one point support, the at least one point support being operable to secure the supply cable on the stand.

18. The X-ray system as claimed in claim 17, wherein the at least one point support is operable to be released without tools.

19. The X-ray system as claimed in claim 14, wherein the U-frame is mounted on the base frame, the U-frame being operable to rotate about a horizontal axis.

20. The X-ray system as claimed in claim 19, wherein the U-frame includes a first limb that supports an X-ray emitter and a second limb that supports the detector support on a free end.

21. The X-ray system as claimed in claim 14,
wherein the support bracket is a U-shaped support bracket, and
wherein the receiving element is mounted on the support plate and is operable to be swiveled about the rotational axis.

* * * * *